United States Patent
Heinemann et al.

(10) Patent No.: US 7,939,467 B2
(45) Date of Patent: *May 10, 2011

(54) 4-(3-AMINOBENZOYL)-1-ETHYLPYRA-ZOLES AND THEIR USE AS HERBICIDES

(75) Inventors: Ines Heinemann, Hofheim (DE); Andreas van Almsick, Karben (DE); Lothar Willms, Hofheim (DE); Monika Schmitt, Frankfurt a. M. Main (DE); Jan Dittgen, Frankfurt a. M. Main (DE); Martin Hills, Idstein (DE); Heinz Kehne, Hofheim (DE); Christopher Rosinger, Hofheim (DE); Dieter Feucht, Eschborn (DE)

(73) Assignee: Bayer CropScience AG, Monheim (DE)

( * ) Notice: Subject to any disclaimer, the term of this patent is extended or adjusted under 35 U.S.C. 154(b) by 368 days.

This patent is subject to a terminal disclaimer.

(21) Appl. No.: 12/101,062

(22) Filed: Apr. 10, 2008

(65) Prior Publication Data

US 2008/0254991 A1    Oct. 16, 2008

(30) Foreign Application Priority Data

Apr. 12, 2007    (EP) .................................... 07007491

(51) Int. Cl.
- A01N 43/56    (2006.01)
- C07D 231/10    (2006.01)
- A61P 13/00    (2006.01)

(52) U.S. Cl. ..................................... 504/282; 548/369.4
(58) Field of Classification Search ........................ None
See application file for complete search history.

(56) References Cited

U.S. PATENT DOCUMENTS

2004/0248736 A1    12/2004    Schmitt et al.

FOREIGN PATENT DOCUMENTS

| | | |
|---|---|---|
| JP | 11-292849 | 10/1999 |
| WO | WO 98/42678 | 10/1998 |

*Primary Examiner* — Kamal A Saeed
(74) *Attorney, Agent, or Firm* — Baker Donelson Caldwell & Berkowitz, PC

(57) ABSTRACT

What is described are 4-(3-aminobenzoyl)-1-ethylpyrazoles of the general formula (I) and their use as herbicides.

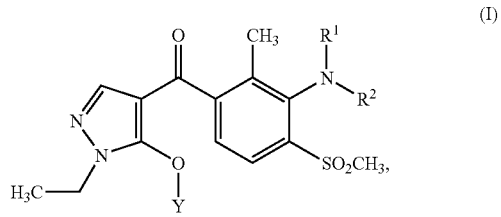

In this general formula (I), $R^1$ and $R^2$ are radicals such as hydrogen and organic radicals, such as alkyl, alkenyl and alkynyl. Y is hydrogen or a protective group, such as tosyl.

20 Claims, No Drawings

4-(3-AMINOBENZOYL)-1-ETHYLPYRAZOLES AND THEIR USE AS HERBICIDES

CROSS REFERENCE TO RELATED APPLICATIONS

This application claims priority from EP 07 007 491.9 filed Apr. 12, 2007, the content of which is incorporated herein.

BACKGROUND OF THE INVENTION

1. Field of the Invention

The invention relates to the technical field of the herbicides, in particular that of the herbicides for the selective control of broad-leaved weeds and weed grasses in crops of useful plants.

2. Description of Related Art

From various publications, it is already known that certain benzoylpyrazoles have herbicidal properties. Thus, US 2004/248736, WO 98/42678 and JP 11292849 each describe 1-alkyl-4-(3-aminobenzoyl)pyrazoles which can be substituted in the 2- and 4-position of the phenyl ring by a large number of different radicals. These documents also disclose the compounds (1-ethyl-5-hydroxy-1H-pyrazol-4-yl)[2-methyl-3-(methylamino)-4-(methylsulfonyl) phenyl]methanone, [3-(ethylamino)-2-methyl-4-(methylsulfonyl)phenyl](1-ethyl-5-hydroxy-1H-pyrazol-4-yl)methanone, (1-ethyl-5-hydroxy-1H-pyrazol-4-yl)[2-methyl-4-(methylsulfonyl)-3-(propylamino)phenyl]methanone, (1-ethyl-5-hydroxy-1H-pyrazol-4-yl){2-methyl-3-[(1-methylethyl)amino]-4-(methyl-sulfonyl)phenyl}methanone, [3-(butylamino)-2-methyl-4-(methylsulfonyl)phenyl](1-ethyl-5-hydroxy-1H-pyrazol-4-yl)methanone, (1-ethyl-5-hydroxy-1H-pyrazol-4-yl){3-[(2-methoxyethyl)amino]-2-methyl-4-(methylsulfonyl)phenyl}methanone, [3-(cyclopropylamino)-2-methyl-4-(methylsulfonyl)phenyl](1-ethyl-5-hydroxy-1H-pyrazol-4-yl)methanone, (1-ethyl-5-hydroxy-1H-pyrazol-4-yl)[2-methyl-4-(methylsulfonyl)-3-(prop-2-en-1-ylamino)phenyl]methanone and [3-(dimethylamino)-2-methyl-4-(methylsulfonyl)phenyl](1-ethyl-5-hydroxy-1H-pyrazol-4-yl)methanone.

However, the herbicidal activity of the compounds known from these publications is frequently insufficient. It is therefore an object of the present invention to provide herbicidally active compounds having herbicidal properties which are better than those of the compounds disclosed in the prior art.

SUMMARY OF THE INVENTION

It has now been found that certain 4-benzoylpyrazoles whose phenyl ring carries a methyl group in the 2-position, a substituted amino group in the 3-position and a methylsulfonyl group in the 4-position are particularly suitable for use as herbicides. Part of the subject matter of the present invention are therefore 4-(3-aminobenzoyl)-1-ethylpyrazoles of the formula (I) or salts thereof

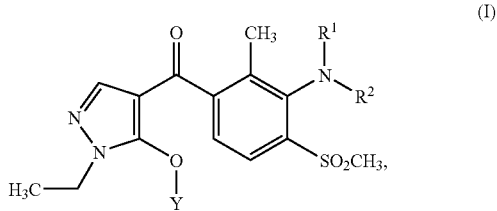

(I)

in which
$R^1$ is hydrogen, $(C_1-C_6)$-alkyl or $(C_1-C_4)$-alkoxy-$(C_1-C_6)$-alkyl,
$R^2$ is $(C_1-C_6)$-alkyl, $(C_2-C_6)$-alkenyl, $(C_2-C_6)$-alkynyl, $(C_1-C_4)$-alkoxy-$(C_1-C_6)$-alkyl, di-$(C_1-C_4)$-alkoxy-$(C_1-C_6)$-alkyl, $(C_1-C_4)$-alkoxy-$(C_1-C_4)$-alkoxy-$(C_1-C_6)$-alkyl, $(C_3-C_6)$-cycloalkyl or $(C_3-C_6)$-cycloalkyl-$(C_1-C_6)$-alkyl;
Y is hydrogen, $(C_1-C_6)$-alkylsulfonyl, $(C_1-C_4)$-alkoxy-$(C_1-C_6)$-alkylsulfonyl, or is phenylsulfonyl, thiophenyl-2-sulfonyl,benzoyl, $(C_1-C_4)$-alkylbenzoyl-$(C_1-C_6)$-alkyl or benzyl, each of which is substituted by m identical or different radicals from the group consisting of halogen, $(C_1-C_4)$-alkyl and $(C_1-C_4)$-alkoxy,
m is 0, 1, 2 or 3,
the intention being for the compounds (1-ethyl-5-hydroxy-1H-pyrazol-4-yl)[2-methyl-3-(methylamino)-4-(methylsulfonyl)phenyl]methanone, [3-(ethylamino)-2-methyl-4-(methylsulfonyl)phenyl](1-ethyl-5-hydroxy-1H-pyrazol-4-yl)methanone, (1-ethyl-5-hydroxy-1H-pyrazol-4-yl)[2-methyl-4-(methylsulfonyl)-3-(propylamino)phenyl] methanone, (1-ethyl-5-hydroxy-1H-pyrazol-4-yl){2-methyl-3-[(1-methylethyl)amino]-4-(methyl-sulfonyl) phenyl}methanone, [3-(butylamino)-2-methyl-4-(methylsulfonyl)phenyl](1-ethyl-5-hydroxy-1H-pyrazol-4-yl)methanone, (1-ethyl-5-hydroxy-1H-pyrazol-4-yl){3-[(2-methoxyethyl)amino]-2-methyl-4-(methylsulfonyl) phenyl}methanone, [3-(cyclopropylamino)-2-methyl-4-(methylsulfonyl)phenyl](1-ethyl-5-hydroxy-1H-pyrazol-4-yl)methanone, (1-ethyl-5-hydroxy-1H-pyrazol-4-yl)[2-methyl-4-(methylsulfonyl)-3-(prop-2-en-1-ylamino) phenyl]methanone and [3-(dimethylamino)-2-methyl-4-(methylsulfonyl)phenyl](1-ethyl-5-hydroxy-1H-pyrazol-4-yl)methanone to be excluded.

DETAILED DESCRIPTION OF A PREFERRED EMBODIMENT

Where Y is hydrogen, the compounds of the formula (I) according to the invention, depending on external conditions, such as solvent and pH, may occur in different tautomeric structures:

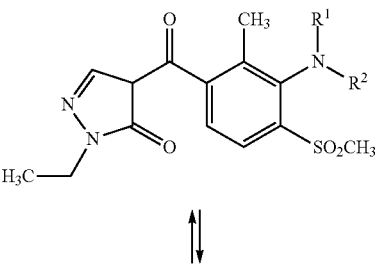

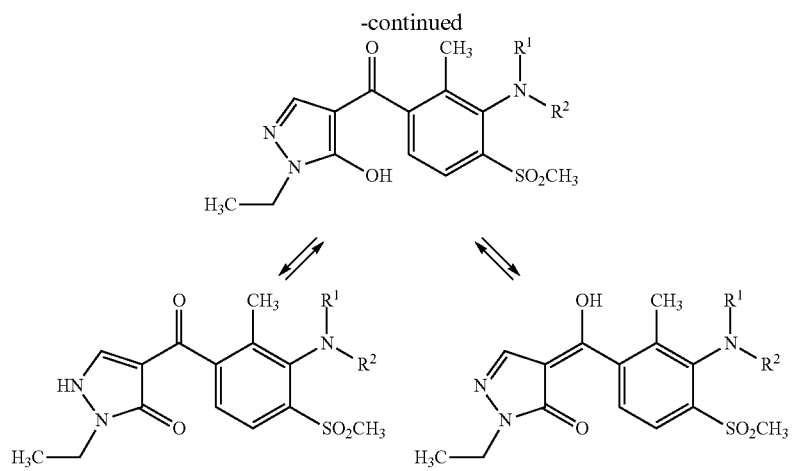

Depending on the nature of the substituents, the compounds of the general formula (I) contain an acidic proton which may be removed by reaction with a base. Suitable bases are, for example, hydrides, hydroxides and carbonates of lithium, sodium, potassium, magnesium and calcium, and also ammonia and organic amines, such as triethylamine and pyridine. It is also possible to form salts by forming adducts with organic acids, such as formic acid or acetic acid, and inorganic acids, such as phosphoric acid, hydrochloric acid or sulfuric acid. Such salts also form part of the subject matter of the invention.

In formula (I) and all subsequent formulae, alkyl radicals with more than two carbon atoms can be straight-chain or branched. Alkyl radicals are, for example, methyl, ethyl, n- or i-propyl, n-, i-, t- or 2-butyl, pentyls, hexyls, such as n-hexyl, i-hexyl and 1,3-dimethylbutyl. Halogen is fluorine, chlorine, bromine or iodine. Tosyl is 4-methylphenylsulfonyl.

If a group is polysubstituted by radicals, this is to be understood as meaning that this group is substituted by one or more identical or different of the radicals mentioned.

Depending on the type and the linkage of the substituents, the compounds of the general formula (I) can exist as stereoisomers. If, for example, one or more asymmetric carbon atoms are present, enantiomers and diastereomers may occur. Stereoisomers can be contained from the mixtures resulting from the preparation by means of customary separation methods, for example by chromatic separation methods. Likewise, stereoisomers may be prepared selectively by using stereoselective reactions employing optically active starting materials and/or auxiliaries. The invention also relates to all stereoisomers and their mixtures which are encompassed by the general formula (I), but not defined specifically.

Preference is given to compounds of the general formula (I) in which $R^1$ is hydrogen or $(C_1-C_4)$-alkyl, $R^2$ is $(C_1-C_4)$-alkyl, $(C_1-C_4)$-alkoxy-$(C_1-C_4)$-alkyl, di-$(C_1-C_2)$-alkoxy-$(C_1-C_4)$-alkyl, $(C_1-C_4)$-alkoxy-$(C_1-C_4)$-alkoxy-$(C_1-C_4)$-alkyl, $(C_3-C_6)$-cycloalkyl or $(C_3-C_6)$-cycloalkyl-$(C_1-C_2)$-alkyl;

Y is hydrogen, $(C_1-C_3)$-alkylsulfonyl, $(C_1-C_2)$-alkoxy-$(C_1-C_4)$-alkylsulfonyl, or is phenylsulfonyl, thiophenyl-2-sulfonyl, benzoyl, $(C_1-C_4)$-alkylbenzoyl-$(C_1-C_6)$-alkyl or benzyl, each of which is substituted by m methyl groups, m is 0 or 1.

Particular preference is given to compounds of the general formula (I) in which $R^1$ is hydrogen or $(C_1-C_4)$-alkyl, $R^2$ is $(C_1-C_4)$-alkyl, $(C_1-C_4)$-alkoxy-$(C_1-C_4)$-alkyl, di-$(C_1-C_2)$-alkoxy-$(C_1-C_4)$-alkyl, $(C_1-C_4)$-alkoxy-$(C_1-C_4)$-alkoxy-$(C_1-C_4)$-alkyl, $(C_3-C_6)$-cycloalkyl or $(C_3-C_6)$-cycloalkyl-$(C_1-C_2)$-alkyl;

Y is hydrogen.

In all the formulae given below, the substituents and symbols have the same meaning as described under formula (I), unless defined otherwise.

Compounds according to the invention in which Y is hydrogen can be prepared, for example, by the process shown in scheme 1 and known from B. S. Jensen, Acta Chem. Scand. 1959, 13, 1668 by base-catalyzed reaction of a benzoyl halide (III) with a pyrazolone (II) or according to the process shown in scheme 2 and known, for example, from EP-A 0 186 117 by base-catalyzed reaction of a benzoyl halide (III) with a pyrazolone (II) and subsequent rearrangement.

Scheme 1

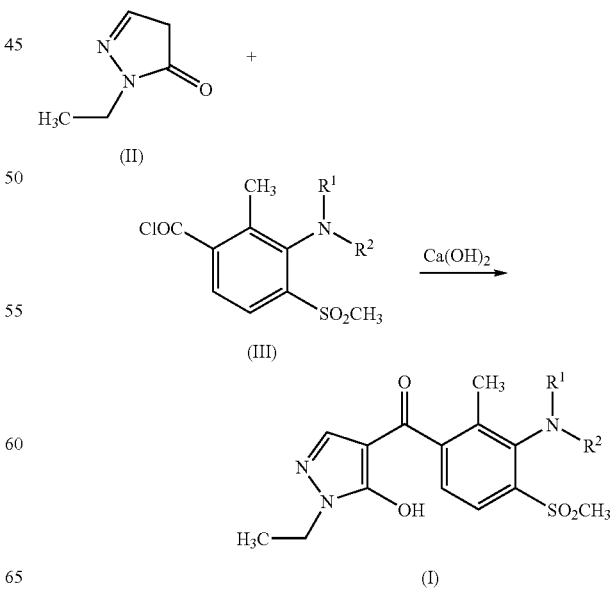

Scheme 2

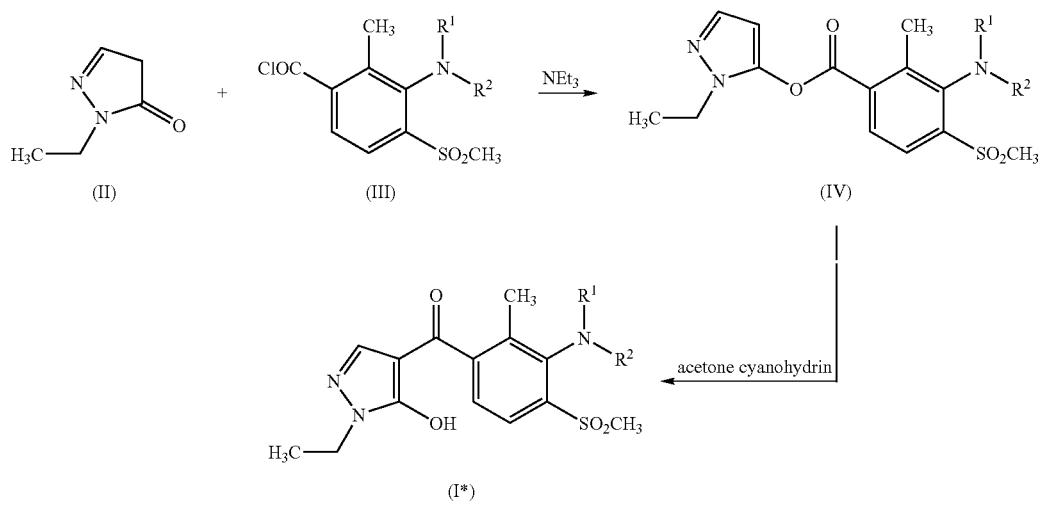

According to scheme 3, compounds according to the invention in which Y has a meaning different from hydrogen are expediently prepared from the compounds obtainable according to scheme 1 or 2, by base-catalyzed reaction with a suitable acylating agent Y—X of the formula (V) in which X is a leaving group, such as halogen. Such methods are known in principle to the person skilled in the art and described, for example, in DE-A 25 13 750.

-continued

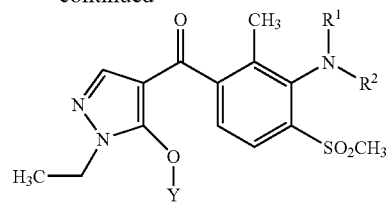

Scheme 3

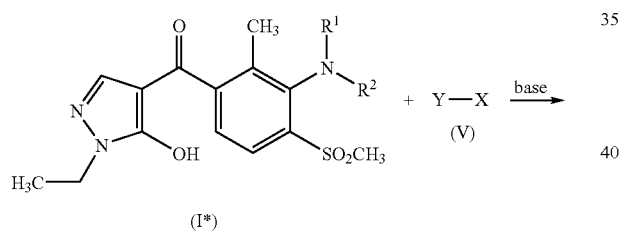

Compounds according to the invention can also be prepared according to the process shown in scheme 4 and known from WO 98/42678 by reacting a pyrazolone (II) with a halobenzoic acid (IIIa) and subsequent reaction with an amine H—NR$^1$R$^2$. Such reactions are known to the person skilled in the art.

Scheme 4

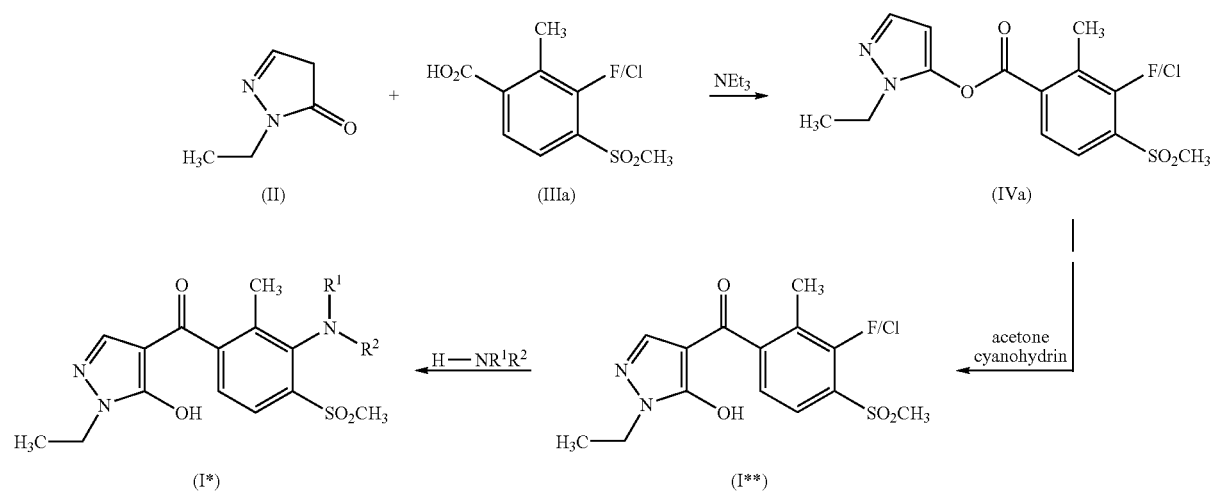

The starting materials used in the above schemes are either commercially available or can be prepared by methods known per se. Thus, the pyrazolones of the formula (II) can be prepared, for example, by the methods described in EP-A 0 240 001 and J. Prakt. Chem. 315, 382, (1973), and the benzoyl chlorides of the formula (III) can be prepared by the methods described in EP-A 0 527 036, WO 98/42678 and in JP 11292849.

The compounds of the formula (I) according to the invention have an excellent herbicidal activity against a broad range of economically important monocotyledonous and dicotyledonous harmful plants. The active substances control perennial weeds equally well which produce shoots from rhizomes, root stocks or other perennial organs and which cannot be easily controlled. In this context, it generally does not matter whether the substances are applied before sowing, pre-emergence or post-emergence. Some representatives of the monocotyledonous and dicotyledonous weed flora which can be controlled by the compounds according to the invention may be mentioned individually as examples, but this is not to be taken to mean a restriction to certain species. The monocotyledonous weed species which are controlled well are, for example, *Avena, Lolium, Alopecurus, Phalaris, Echinochloa, Digitaria, Setaria* and *Cyperus* species from the annual group, and *Agropyron, Cynodon, Imperata* and *Sorghum* or else perennial *Cyperus* species amongst the perennial species. In the case of dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* from the annual group, and *Convolvulus, Cirsium, Rumex* and *Artemisia* among the perennial weeds. Harmful plants which are found under the specific culture conditions of rice, such as, for example, *Echinochloa, Sagittaria, Alisma, Eleocharis, Scirpus* and *Cyperus* are also controlled outstandingly well by the active substances according to the invention. If the compounds according to the invention are applied to the soil surface prior to germination, then either emergence of the weed seedlings is prevented completely, or the weeds grow until they have reached the cotyledon stage but growth then comes to a standstill and, after a period of three to four weeks, the plants eventually die completely. When the active substances are applied post-emergence to the green parts of the plants, growth also stops drastically very soon after the treatment, and the weeds remain at the growth stage of the time of application, or, after a certain period of time, they die completely so that competition by the weeds, which is detrimental for the crop plants, is thus eliminated at a very early stage and in a sustained manner. In particular, the compounds according to the invention have an outstanding action against *Apera spica venti, Chenopodium album, Lamium purpureum, Polygonum convulvulus, Stellaria media, Veronica hederifolia, Veronica persica* and *Viola tricolor.*

Although the compounds according to the invention have an outstanding herbicidal activity against monocotyledonous and dicotyledonous weeds, crop plants of economically important crops such as, for example, wheat, barley, rye, rice, corn, sugar beet, cotton and soybeans, only suffer negligible damage, if any. In particular, they are outstandingly well tolerated in cereals, such as wheat, barley and corn, in particular wheat. This is why the present compounds are highly suitable for the selective control of undesired vegetation in stands of agricultural useful plants or of ornamentals.

Owing to their herbicidal properties, the active substances can also be employed for controlling harmful plants in crops of known plants or genetically modified plants which are yet to be developed. As a rule, the transgenic plants are distinguished by particularly advantageous properties, for example by resistances to certain pesticides, especially certain herbicides, by resistances to plant diseases or causative organisms of plant diseases, such as certain insects or microorganisms such as fungi, bacteria or viruses. Other particular properties concern for example the harvested material with regard to quantity, quality, shelf life, composition and specific constituents. Thus, transgenic plants are known which have an increased starch content or whose starch quality has been modified, or whose fatty acid composition in the harvested material is different.

The compounds of the formula (I) according to the invention or their salts are preferably employed in economically important transgenic crops of useful plants and ornamentals, for example cereals such as wheat, barley, rye, oats, millet, rice, cassava and corn, or else crops of sugar beet, cotton, soybeans, oilseed rape, potato, tomato, pea and other vegetables. The compounds of the formula (I) can preferably be employed as herbicides in crops of useful plants which are resistant, or have been genetically modified to be resistant, to the phytotoxic effects of the herbicides.

Conventional routes for the generation of novel plants which have modified properties compared with existing plants are, for example, traditional breeding methods and the generation of mutants. Alternatively, novel plants with modified properties can be generated with the aid of recombinant methods (see, for example, EP-A-0221044, EP-A-0131624). For example, several cases of the following have been described:

recombinant modifications of crop plants for the purposes of modifying the starch synthesized in the plants (for example WO 92/11376, WO 92/14827, WO 91/19806), transgenic crop plants which exhibit resistances to certain herbicides of the glufosinate type (cf. eg. EP-A-0242236, EP-A-242246), glyphosate type (WO 92/00377) or of the sulfonylurea type (EP-A-0257993, U.S. Pat. No. 5,013,659)

transgenic crop plants, for example cotton, with the ability to produce *Bacillus thuringiensis* toxins (Bt toxins), which make the plants resistant to certain pests (EP-A-0142924, EP-A-0193259), transgenic crop plants with a modified fatty acid composition (WO 91/13972).

A large number of techniques in molecular biology, with the aid of which novel transgenic plants with modified properties can be generated, are known in principle; see, for example, Sambrook et al., 1989, Molecular Cloning, A Laboratory Manual, $2^{nd}$ Ed., Cold Spring Harbor Laboratory Press, Cold Spring Harbor, N.Y.; or Winnacker "Gene und Klone" [Genes and Clones], VCH Weinheim $2^{nd}$ Edition 1996 or Christou, "Trends in Plant Science" 1 (1996) 423-431.

To carry out such recombinant manipulations, nucleic acid molecules can be introduced into plasmids which permit a mutagenesis or a sequence alteration by recombination of DNA sequences. With the aid of the abovementioned standard methods, it is possible, for example, to carry out base substitutions, to remove part sequences or to add natural or synthetic sequences. The fragments can be provided with adapters or linkers to link the DNA fragments to each other.

Plant cells with a reduced activity of a gene product can be obtained, for example, by expressing at least one corresponding antisense RNA, a sense RNA for achieving a cosuppression effect, or by expressing at least one suitably constructed ribozyme which specifically cleaves transcripts of the abovementioned gene product.

To this end, it is possible, on the one hand, to use DNA molecules which encompass all of the coding sequence of a gene product including any flanking sequences which may be present, but also DNA molecules which only encompass portions of the coding sequence, it being necessary for these portions to be so long as to cause an antisense effect in the cells. Another possibility is the use of DNA sequences which have a high degree of homology with the coding sequences of a gene product, but are not completely identical.

When expressing nucleic acid molecules in plants, the protein synthesized may be localized in any desired compartment of the plant cell. However, to achieve localization in a particular compartment, the coding region can, for example, be linked to DNA sequences which ensure localization in a particular compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated by known techniques to give intact plants. In principle, the transgenic plants can be plants of any desired plant species, i.e. both monocotyledonous and dicotyledonous plants. Thus, transgenic plants can be obtained which exhibit modified properties owing to the overexpression, suppression or inhibition of homologous (=natural) genes or gene sequences or expression of heterologous (=foreign) genes or gene sequences.

When using the active substances according to the invention in transgenic crops, effects are frequently observed in addition to the effects against harmful plants to be observed in other crops, which are specific for the application in the transgenic crop in question, for example a modified or specifically widened weed spectrum which can be controlled, modified application rates which may be employed for the application, preferably good combining ability with the herbicides to which the transgenic crop is resistant, and an effect on the growth and yield of the transgenic crop plants. The invention therefore also relates to the use of the compounds according to the invention as herbicides for controlling harmful plants in transgenic crop plants.

The substances according to the invention additionally have outstanding growth-regulatory properties in crop plants. They engage in the plants' metabolism in a regulatory fashion and can thus be employed for the targeted control of plant constituents and for facilitating harvesting, such as, for example, triggering desiccation and stunted growth. Moreover, they are also suitable for generally controlling and inhibiting undesired vegetative growth without destroying the plants in the process. Inhibiting the vegetative growth plays an important role in many monocotyledonous and dicotyledonous crops since lodging can be reduced, or prevented completely, hereby.

The compounds according to the invention can be employed in the form of wettable powders, emulsifiable concentrates, sprayable solutions, dusts or granules in the customary preparations. The invention therefore furthermore relates to herbicidal compositions comprising compounds of the formula (I). The compounds of the formula (I) can be formulated in various ways, depending on the prevailing biological and/or chemico-physical parameters. Examples of suitable formulations which are possible are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for spreading and soil application, granules (GR) in the form of microgranules, spray granules, coated granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Engineering], Volume 7, C. Hauser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4th Ed. 1986.

Wettable powders are preparations which are uniformly dispersible in water and which, in addition to the active substance, also contain ionic and/or nonionic surfactants (wetters, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium 2,2'-dinaphthylmethane-6,6'-disulfonate, sodium lignosulfonate, sodium dibutylnaphthalenesulfonate or else sodium oleoylmethyltaurate, in addition to a diluent or inert substance. To prepare the wettable powders, the herbicidal active substances are ground finely, for example in customary equipment such as hammer mills, blowing mills and air-jet mills, and simultaneously or subsequently mixed with the formulation auxiliaries.

Emulsifiable concentrates are prepared by dissolving the active substance in an organic solvent, e.g. butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which can be used are: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials, for example talc, natural clays such as kaolin, bentonite and pyrophyllite, or diatomaceous earth.

Suspension concentrates can be water-based or oil-based. They can be prepared for example by wet-grinding by means of customary bead mills, if appropriate with addition of surfactants, as have already been mentioned for example above in the case of the other formulation types.

Emulsions, for example oil-in-water emulsions (EW), can be prepared for example by means of stirrers, colloid mills and/or static mixers using aqueous organic solvents and, if appropriate, surfactants as have already been mentioned for example above in the case of the other formulation types.

Granules can be prepared either by spraying the active substance onto adsorptive, granulated inert material or by applying active substance concentrates to the surface of carriers such as sand, kaolinites or granulated inert material with the aid of adhesives, for example polyvinyl alcohol, sodium polyacrylate or else mineral oils. Suitable active substances can also be granulated in the fashion which is conventional for the production of fertilizer granules, if desired as a mixture with fertilizers.

Water-dispersible granules are generally prepared by customary methods such as spray drying, fluidized-bed granulation, disk granulation, mixing with high-speed stirrers and extrusion without solid inert material.

To prepare disk granules, fluidized-bed granules, extruder granules and spray granules, see, for example methods in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pp. 8-57.

For further details on the formulation of crop protection agents see, for example G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical preparations comprise 0.1 to 99% by weight, in particular 0.1 to 95% by weight, of active substance of the formula (I). In wettable powders, the active substance concentration is, for example, approximately 10 to 90% by weight, the remainder to 100% by weight being composed of customary formulation constituents. In the case of emulsifiable concentrates, the active substance concentration can amount to approximately 1 to 90, preferably 5 to 80% by weight. Formulations in the form of dusts comprise 1 to 30% by weight of active substance, preferably in most cases 5 to 20% by weight of active substance, and sprayable solutions comprise approximately 0.05 to 80, preferably 2 to 50% by weight of active substance. In the case of water-dispersible granules, the active substance content depends partly on whether the active compound is in liquid or solid form and on the granulation auxiliaries, fillers and the like which are being used. In the case of the water-dispersible granules, for example, the active substance content is between 1 and 95% by weight, preferably between 10 and 80% by weight.

In addition, the active substance formulations mentioned comprise, if appropriate, the tackifiers, wetters, dispersants, emulsifiers, penetrants, preservatives, antifreeze agents, solvents, fillers, carriers, colorants, antifoams, evaporation inhibitors, and pH and viscosity regulators which are conventional in each case.

Based on these formulations, it is also possible to prepare combinations with other pesticidally active substances such as, for example, insecticides, acaricides, herbicides, fungicides, and with safeners, fertilizers and/or growth regulators, for example in the form of a readymix or a tank mix.

Active substances which can be employed in combination with the active substances according to the invention in mixed formulations or in the tank mix are, for example, known active substances as are described, for example, in Weed Research 26, 441-445 (1986) or "The Pesticide Manual", 11th edition, The British Crop Protection Council and the Royal Soc. of Chemistry, 1997 and literature cited therein. Known herbicides which must be mentioned, and can be combined with the compounds of the formula (I), are, for example, the following active substances (note: the compounds are either designated by the common name according to the International Organization for Standardization (ISO) or using the chemical name, if appropriate together with a customary code number): acetochlor; acifluorfen; aclonifen; AKH 7088, i.e. [[[1-[5-[2-chloro-4-(trifluoromethyl)-phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazine; azimsulfurone (DPX-A8947); aziprotryn; barban; BAS 516 H, i.e. 5-fluorine-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone; CDAA, i.e. 2-chloro-N,N-di-2-propenylacetamide; CDEC, i.e. 2-chloroallyl diethyldithiocarbamate; chlomethoxyfen; chloramben; chlorazifop-butyl, chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (for example butylester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (for example ethylester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flucarbazoue; flufenacet; flumetsulam; flumeturon; flumiclorac and its esters (for example pentylester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; foramsulfuron; fosamine; furyloxyfen; glufosinate; glyphosate; halosafen; halosulfuron and its esters (for example methylester, NC-319); haloxyfop and its esters; haloxyfop-P (=R-haloxyfop) and its esters; hexazinone; imazapyr; imazamethabenz-methyl; imazaquin and salts such as the ammonium salt; ioxynil; imazethamethapyr; imazethapyr; imazosulfuron; iodosulfuron-methyl-sodium; isocarbamid; isopropalin; isoproturon; isouron; isoxaben; isoxapyrifop; karbutilate; lactofen; lenacil; linuron; MCPA; MCPB; mecoprop; mefenacet; mefluidid; mesosulfuron; mesotrione; metamitron; metazachlor; metham; methabenzthiazuron; methazole; methoxyphenone; methyidymron; metabenzuron, methobenzuron; metobromuron; metolachlor; metosulam (XRD 511); metoxuron; metribuzin; metsulfuron-methyl; MH; molinate; monalide; monolinuron; monuron;

monocarbamide dihydrogensulfate; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; pinoxaden; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propoxycarbazone; propyzamide; prosulfalin; prosulfocarb; prosulfuron (CGA-152005); prynachlor; pyrazolinate; pyrazon; pyrasulfotole; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivatives for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy] propanoic acid and its methyl ester; sulcotrione; sulfentrazon (FMC-97285, F-6285); sulfazuron; sulfometuron-methyl; sulfosate (ICI-A0224); TCA; tebutam (GCP-5544); tebuthiuron; tembotrione; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiencarbazone; thiazopyr (Mon-13200); thidiazimin (SN-24085); thiobencarb; thifensulfuron-methyl; tiocarbazil; tralkoxydim; tri-allate; triasulfuron; triazofenamide; tribenuron-methyl; triclopyr; tridiphane; trietazine; trifluralin; triflusulfuron and esters (for example methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations, which are present in commercially available form, are if appropriate diluted in the customary manner, for example using water in the case of wettable powders, emulsifiable concentrates, dispersions and water-dispersible granules. Preparations in the form of dusts, soil granules, granules for spreading and sprayable solutions are usually not diluted any further with other inert substances prior to use.

The application rate required of the compounds of the formula (I) varies with the external conditions such as, inter alia, temperature, humidity and the nature of the herbicide used. It can vary within wide limits, for example between 0.001 and 1.0 kg/ha or more of active substance, but it is preferably between 0.005 and 750 g/ha.

The examples which follow illustrate the invention.

A. CHEMICAL EXAMPLES

Preparation of 4-[3-isobutylamino-2-methyl-4-(methylsulfonyl)benzoyl]-1-ethyl-5-hydroxypyrazole Step 1:
3-Isobutylamino-2-methyl-4-(methylsulfonyl)benzoic acid 2.0 g (9 mmol) of 3-fluoro-2-methyl-4-(methylsulfonyl) benzoic acid were dissolved in 26.5 ml (267 mmol) of isobutylamine. The mixture was heated at reflux with stirring for 8 days, cooled to RT, acidified with 10% strength sulfuric acid and extracted twice with ethyl acetate. The combined organic phases were dried over $MgSO_4$, and the solvent was removed under reduced pressure. This gave 2.4 g of a colorless solid of a purity of 98%.

$^1$H-NMR: δ[$CDCl_3$] 1.05 (d,6H), 1.90-2.00 (m,1H), 2.53 (s,3H), 2.98 (d,2H), 3.09 (s,3H), 7.55 (d,1H), 7.80 (d,1H)

Step 2: 4-[3-Isobutylamino-2-methyl-4-(methylsulfonyl)benzoyl]-1-ethyl-5-hydroxypyrazole Under nitrogen, 0.43 g (1.5 mmol) of 3-isobutylamino-2-methyl-4-(methyl-sulfonyl)benzoic acid, 0.22 g (2.0 mmol) of 1-ethyl-5-hydroxypyrazole and 0.35 g (1.8 mmol) of 1-(3-dimethylaminopropyl)-3-ethylcarbodiimide hydrochloride were dissolved in dry acetonitrile. The mixture was stirred at RT for 1 day and allowed to stand for 2 days. 0.42 ml (3.0 mmol) of $NEt_3$, 0.08 ml (0.6 mmol) of $Me_3SiCN$ and a spatula tip of KCN were added, and the mixture was stirred at RT for 2 days. The solvent was removed, and the residue was taken up in $CH_2Cl_2$ and 10% strength $H_2SO_4$. The organic phase was separated off and dried over $MgSO_4$, and the solvent was removed under reduced pressure. The residue was crystallized from acetonitrile. This gave 0.16 g of a red solid of a purity of 96%.

$^1$H-NMR: δ[$CDCl_3$] 1.05 (d,6H), 1.47 (t,3H), 1.88-2.01 (m,1H), 2.32 (s,3H), 3.03 (d,2H), 3.11 (s,3H), 4.08 (q,2H), 7.05 (d,1H), 7.37 (s,1H), 7.81 (d,1H).

Preparation of 4-[3-(2,2-diethoxyethyl)amino-2-methyl-4-(methylsulfonyl)benzoyl]-1-ethyl-5-hydroxypyrazole Step 1: 3-(2,2-Diethoxyethyl)amino-2-methyl-4-(methylsulfonyl)benzoic acid 5.1 g (22 mmol) of 3-fluoro-2-methyl-4-(methylsulfonyl) benzoic acid were dissolved in 30 ml (218 mmol) of aminoacetaldehyde diethyl acetal. The mixture was heated at 120° C. with stirring for 2 days, cooled to RT, acidified with 10% strength $H_2SO_4$ and extracted twice with ethyl acetate. The combined organic phases were dried over $MgSO_4$, and the solvent was removed under reduced pressure. This gave 4.0 g of a yellow oil of a purity of 91%.

$^1$H-NMR: δ[$CDCl_3$] 1.24 (t,6H), 2.53 (s,3H), 3.19 (s,3H), 3.30 (d,2H), 3.55-3.66 (m,2H), 3.70-3.82 (m,2H), 4.69 (t,1H), 7.55 (d,1H), 7.81 (d,1H)

Step 2: 4-[3-(2,2-Diethoxyethyl)amino-2-methyl-4-(methylsulfonyl)benzoyl]-1-ethyl-5-hydroxypyrazole Under nitrogen, 0.38 g (1.1 mmol) of 3-(2,2-diethoxyethyl)amino-2-methyl-4-(methyl-sulfonyl)benzoic acid, 0.16 g (1.4 mmol) of 5-hydroxy-1-methylpyrazole and 0.25 g (1.3 mmol) of 1-(3-dimethylaminopropyl)-3-ethylcarbodiimide hydrochloride were dissolved in dry $CH_3CN$. The mixture was stirred at RT for 1 day and allowed to stand for 2 days. 0.31 ml (2.2 mmol) of $NEt_3$, 0.06 ml (0.4 mmol) of $Me_3SiCN$ and a spatula tip of KCN were added, and the mixture was stirred at RT for 2 days. The solvent was removed under reduced pressure, and the residue was taken up in $CH_2Cl_2$ and 10% strength $H_2SO_4$. The organic phase was removed and dried over $MgSO_4$, and the solvent was removed under reduced pressure. The residue were purified by preparative HPLC. This gave 0.14 g of a red oil in a purity of 93%.

¹H-NMR: δ[CDCl₃] 1.24 (t,6H), 1.46 (t,3H), 2.33 (s,3H), 3.20 (s,3H), 3.36 (d,2H), 3.54-3.66 (m,2H), 3.68-3.80 (m,2H), 4.08 (q,2H), 4.68 (t,1H), 7.08 (d,1H), 7.37 (s,1H), 7.84 (d,1H)

Preparation of 2-{(1-ethyl-4-[3-(3-methoxypropyl)amino-2-methyl-4-(methylsulfonyl)benzoyl]-1H-pyrazol-5-yl)oxy}-1-phenylethanone Under nitrogen, 0.30 g (1.4 mmol) of 2-bromoacetophenone and 0.52 g (3.8 mmol) of potassium carbonate were added to a solution of 0.50 g (1.3 mmol) of 4-{[3-(3-methoxypropyl)amino]-2-methyl-4-(methylsulfonyl)benzoyl}-1-ethyl-5-hydroxypyrazole in acetonitrile. The mixture was stirred at RT for 4 h, the solvent was removed under reduced pressure and the residue was taken up in water and ethyl acetate. The organic phase was separated off, the aqueous phase was extracted once with ethyl acetate and the combined organic phases were dried over MgSO₄. The solvent was removed under reduced pressure. The residue was purified by column chromatography on silica gel. This gave 0.60 g of a yellow oil in a purity of 95%.

¹H-NMR: δ[CDCl₃] 1.51 (t,3H), 1.87-1.97 (m,2H), 2.17 (s,3H), 2.42 (s,3H), 3.11 (s,3H), 3.25 (t,2H), 3.34 (s,3H), 3.53 (t,2H), 4.29 (q,2H), 6.14 (s,2H), 6.92 (d,1H), 7.24 (s,1 H), 7.29 (d,2H), 7.75 (d,1H), 7.82 (d,2H)

The examples given in the tables which follow were prepared analogously to the methods mentioned above, or can be obtained analogously to the methods mentioned above. These compounds are particularly preferred.

The abbreviations used denote:

| | | | |
|---|---|---|---|
| Bn = Benzyl | Bu = Butyl | Bz = Benzoyl | Et = Ethyl |
| Me = Methyl | Ph = Phenyl | Pr = Propyl | t = tertiary |
| c = cyclo | i = iso | s = secondary | |

TABLE A

Compounds according to the invention of the general formula (I)

| No. | R¹ | R² | Y | Physical data: ¹H-NMR: δ [CDCl₃] |
|---|---|---|---|---|
| 1 | H | s-Bu | H | 0.99 (t, 3 H), 1.16 (d, 3 H), 1.47 (t, 3 H), 1.45-1.56 (m, 1 H), 1.60-1.71 (m, 1 H), 2.28 (s, 3 H), 3.10 (s, 3 H), 3.50-3.61 (m, 1 H), 4.08 (q, 2 H), 7.01 (d, 1 H), 7.36 (s, 1 H), 7.80 (d, 1 H) |
| 2 | H | i-Bu | H | 1.05 (d, 6H), 1.47 (t, 3 H), 1.88-2.01 (m, 1 H), 2.32 (s, 3 H), 3.03 (d, 2 H), 3.11 (s, 3 H), 4.08 (q, 2 H), 7.05 (d, 1 H), 7.37 (s, 1 H), 7.81 (d, 1 H) |
| 3 | H | CH₂-c-Pr | H | 0.25-0.31 (m, 2 H), 0.58-0.63 (m, 2 H), 1.05-1.16 (m, 1 H), 1.46 (t, 3 H), 2.32 (s, 3 H), 3.09 (d, 2 H), 3.14 (s, 3 H), 4.08 (q, 2 H), 7.05 (d, 1 H), 7.37 (s, 1 H), 7.82 (d, 1 H) |
| 4 | H | (CH₂)₂O-Et | H | 1.24 (t, 3 H), 1.46 (t, 3 H), 2.32 (s, 3 H), 3.21 (s, 3 H), 3.39-3.44 (m, 2 H), 3.57 (q, 2 H), 3.64-3.69 (m, 2 H), 4.08 (q, 2 H), 7.08 (d, 1 H), 7.37 (s, 1 H), 7.85 (d, 1 H) |
| 5 | H | (CH₂)₃O-Me | H | 1.46 (t, 3 H), 1.90-1.99 (m, 2 H), 2.33 (s, 3 H), 3.12 (s, 3 H), 3.30 (t, 2 H), 3.36 (s, 3 H), 3.55 (t, 2 H), 4.08 (q, 2 H), 7.08 (d, 1 H), 7.37 (s, 1 H), 7.84 (d, 1 H) |
| 6 | H | (CH₂)₃O-Et | H | 1.21 (t, 3 H), 1.46 (t, 3 H), 1.90-1.99 (m, 2 H), 2.33 (s, 3 H), 3.14 (s, 3 H), 3.32 (t, 2 H), 3.52 (q, 2 H), 3.58 (t, 2 H), 4.08 (q, 2 H), 7.08 (d, 1 H), 7.38 (s, 1 H), 7.84 (d, 1 H) |
| 7 | H | (CH₂)₂O—(CH₂)₂O-Me | H | 1.46 (t, 3 H), 2.32 (s, 3 H), 3.21 (s, 3 H), 3.38 (s, 3 H), 3.41-3.47 (m, 2 H), 3.55-3.60 (m, 2 H), 3.65-3.70 (m, 2 H), 3.70-3.75 (m, 2 H), 4.08 (q, 2 H), 7.08 (d, 1 H), 7.38 (s, 1 H), 7.85 (d, 1 H) |
| 8 | H | (CH₂)CH(OMe)₂ | H | 1.46 (t, 3 H), 2.33 (s, 3 H), 3.20 (s, 3 H), 3.37 (d, 2 H), 3.43 (s, 6H), 4.08 (q, 2 H), 4.55 (t, 1 H), 7.08 (d, 1 H), 7.37 (s, 1 H), 7.84 (d, 1 H) |
| 9 | H | (CH₂)CH(OEt)₂ | H | 1.24 (t, 6 H), 1.46 (t, 3 H), 2.33 (s, 3 H), 3.20 (s, 3 H), 3.36 (d, 2 H), 3.54-3.66 (m, 2 H), 3.68-3.80 (m, 2 H), 4.08 (q, 2 H), 4.68 (t, 1 H), 7.08 (d, 1 H), 7.37 (s, 1 H), 7.84 (d, 1 H) |
| 10 | Me | Et | H | 1.22 (t, 3 H), 1.46 (t, 3 H), 2.36 (s, 3 H), 2.88 (s, 3 H), 3.08-3.34 (m, 2 H), 3.32 (s, 3 H), 4.08 (q, 2 H), 7.34 (s, 1 H), 7.40 (d, 1 H), 8.05 (d, 1 H) |

TABLE A-continued

Compounds according to the invention of the general formula (I)

| No. | R¹ | R² | Y | Physical data: ¹H-NMR: δ [CDCl₃] |
|---|---|---|---|---|
| 11 | Me | CH₂-c-Pr | H | 0.11-0.18 (m, 1 H), 0.18-0.28 (m, 1 H), 0.43-0.53 (m, 1 H), 0.59-0.68 (m, 1 H), 1.08-1.17 (m, 1 H), 1.47 (t, 3 H), 2.34 (s, 3 H), 2.67-2.75 (m, 1 H), 2.99 (s, 3 H), 3.28-3.36 (m, 1 H), 3.37 (s, 3 H), 4.08 (q, 2 H), 7.34 (s, 1 H), 7.40 (d, 1 H), 8.05 (d, 1 H) |
| 12 | Me | (CH₂)₂O-Et | H | 1.18 (t, 3 H), 1.46 (t, 3 H), 2.39 (s, 3 H), 2.96 (s, 3 H), 3.22-3.33 (m, 1 H), 3.38 (s, 3 H), 3.40-3.49 (m, 1 H), 3.49 (q, 2 H), 3.68-3.74 (m, 2 H), 4.09 (q, 2 H), 7.35 (s, 1 H), 7.40 (d, 1 H), 8.05 (d, 1 H) |
| 13 | Me | (CH₂)₃O-Me | H | 1.47 (t, 3 H), 1.89-2.03 (m, 2 H), 2.38 (s, 3 H), 2.91 (s, 3 H), 3.07-3.21 (m, 1 H), 3.24-3.34 (m, 1 H), 3.30 (s, 3 H), 3.32 (s, 3 H), 3.38-3.46 (m, 2 H), 4.08 (q, 2 H), 7.34 (s, 1 H), 7.40 (d, 1 H), 8.05 (d, 1 H) |
| 14 | H | (CH₂)₃O-Me | n-Pr-SO₂ | 1.17 (t, 3 H), 1.51 (t, 3 H), 1.89-1.99 (m, 2 H), 2.04-2.18 (m, 2 H), 2.27 (s, 3 H), 3.13 (s, 3 H), 3.29 (t, 2 H), 3.37 (s, 3 H), 3.54 (t, 2 H), 3.66-3.74 (m, 2 H), 4.22 (q, 2 H), 5.58 (br, 1 H), 7.00 (d, 1 H), 7.50 (s, 1 H), 7.82 (d, 1 H) |
| 15 | H | (CH₂)₃O-Me | Me-O(CH₂)₂—SO₂ | 1.51 (t, 3 H), 1.88-2.00 (m, 2 H), 2.28 (s, 3 H), 3.13 (s, 3 H), 3.29 (t, 2 H), 3.37 (s, 3 H), 3.45 (s, 3 H), 3.55 (t, 2 H), 3.99-4.12 (m, 4 H), 4.23 (q, 2 H), 7.01 (d, 1 H), 7.49 (s, 1 H), 7.82 (d, 1 H) |
| 16 | H | (CH₂)₃O-Me | Ph-SO₂ | 1.50 (t, 3 H), 1.87-2.00 (m, 2 H), 2.24 (s, 3 H), 3.12 (s, 3 H), 3.28 (t, 2 H), 3.37 (s, 3 H), 3.55 (t, 2 H), 4.16 (q, 2 H), 5.57 (br, 1 H), 6.87 (d, 1 H), 7.55-7.67 (m, 3 H), 7.68-7.80 (m, 2 H), 7.92-7.99 (m, 2 H) |
| 17 | H | (CH₂)₂O-Me | 4-Me-Ph-SO₂ | 1.49 (t, 3 H), 1.88-1.99 (m, 2 H), 2.24 (s, 3 H), 2.47 (s, 3 H), 3.11 (s, 3 H), 3.26 (t, 2 H), 3.37 (s, 3 H), 3.54 (t, 2 H), 4.16 (q, 2 H), 5.54 (br, 1 H), 6.87 (d, 1 H), 7.38 (d, 2 H), 7.61 (s, 1 H), 7.71 (d, 1 H), 7.80 (d, 2 H) |
| 18 | H | (CH₂)₂O-Me | thiophene-SO₂ | 1.49 (t, 3 H), 1.88-1.99 (m, 2 H), 2.24 (s, 3 H), 3.12 (s, 3 H), 3.28 (t, 2 H), 3.37 (s, 3 H), 3.54 (t, 2 H), 4.16 (q, 2 H), 6.91 (d, 1 H), 7.18-7.22 (m, 1 H), 7.58 (s, 1 H), 7.74 (d, 1 H), 7.82-7.87 (m, 2 H) |
| 19 | H | (CH₂)₃O-Me | Ph-C(O) | 1.47 (t, 3 H), 1.82-1.92 (m, 2 H), 2.24 (s, 3 H), 2.92 (s, 3 H), 3.17 (t, 2 H), 3.36 (s, 3 H), 3.50 (t, 2 H), 4.05 (q, 2 H), 5.36 (br, 1 H), 6.95 (d, 1 H), 7.50 (t, 2 H), 7.63 (d, 1 H), 7.68 (t, 1 H), 7.84 (s, 1 H), 7.97 (d, 2 H) |
| 20 | H | (CH₂)₃O-Me | 4-Me-Ph-C(O)—CH₂ | 1.51 (t, 3 H), 1.87-1.97 (m, 2 H), 2.17 (s, 3 H), 2.42 (s, 3 H), 3.11 (s, 3 H), 3.25 (t, 2 H), 3.34 (s, 3 H), 3.53 (t, 2 H), 4.29 (q, 2 H), 6.14 (s, 2 H), 6.92 (d, 1 H), 7.24 (s, 1 H), 7.29 (d, 2 H), 7.75 (d, 1 H), 7.82 (d, 2 H) |

B. FORMULATION EXAMPLES

1. Dust

A dust is obtained by mixing 10 parts by weight of a compound of general formula (I) and 90 parts by weight of talc as inert substance and comminuting the mixture in a hammer mill.

2. Dispersible Powder

A wettable powder which is readily dispersible in water is obtained by mixing 25 parts by weight of a compound of general formula (I), 64 parts by weight of kaolin-containing quartz as inert material, 10 parts by weight of potassium lignosulfonate and 1 part by weight of sodium oleoylmethyltauride as wetter and dispersant, and grinding the mixture in a pinned-disk mill.

3. Dispersion Concentrate

A dispersion concentrate which is readily dispersible in water is obtained by mixing 20 parts by weight of a compound of general formula (I), 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.), and grinding the mixture in a ball mill to a fineness of below 5 microns.

4. Emulsifiable Concentrate

An emulsifiable concentrate is obtained from 15 parts by weight of a compound of general formula (I), 75 parts by weight of cyclohexanone as solvent and 10 parts by weight of oxethylated nonylphenol as emulsifier.

5. Water-dispersible Granules

Water-dispersible granules are obtained by mixing

| | |
|---|---|
| 75 parts by weight of | a compound of general formula (I), |
| 10 parts by weight of | calcium lignosulfonate, |
| 5 parts by weight of | sodium lauryl sulfate, |
| 3 parts by weight of | polyvinyl alcohol and |
| 7 parts by weight of | kaolin, | grinding the mixture in a pinned-disk mill and granulating the powder in a fluidized bed by spraying on water as granulation liquid.

Water-dispersible granules are also obtained by homogenizing and precomminuting, in a colloid mill,

| | |
|---|---|
| 25 parts by weight of | a compound of general formula (I), |
| 5 parts by weight of | sodium 2,2'-dinaphthylmethane-6,6'-disulfonate, |
| 2 parts by weight of | sodium oleoylmethyltauride, |
| 1 parts by weight of | polyvinyl alcohol, |
| 17 parts by weight of | calcium carbonate and |
| 50 parts by weight of | water, | subsequently grinding the mixture in a bead mill, and atomizing and drying the resulting suspension in a spray tower by means of a single-substance nozzle.

C. BIOLOGICAL EXAMPLES

1. Pre-emergence Herbicidal Action Against Harmful Plants

Seeds or rhizome pieces of mono- and dicotyledonous harmful plants are placed in sandy loam in pots of a diameter of 9 to 13 cm and covered with soil. The herbicides, formulated as emulsifiable concentrates or dusts, are applied to the surface of the covering soil in the form of aqueous dispersions or suspensions or emulsions at an application rate of 300 to 800 l of water/ha (converted), at various dosages. For further cultivation of the plants, the pots are then kept in a greenhouse under optimum conditions. The visual scoring of the damage to the harmful plants is carried out 3-4 weeks after the treatment. As shown by the results of these comparative tables, the selected compounds according to the invention have better herbicidal activity against a broad spectrum of economically important mono- and dicotyledonous harmful plants than the compounds disclosed in the prior art.

2. Post-emergence Herbicidal Action Against Harmful Plants

Seeds of mono- and dicotyledonous harmful plants are placed in sandy loam in cardboard pots, covered with soil and grown in the greenhouse under good growth conditions. Two to three weeks after sowing, the test plants are treated at the three-leaf stage. The compounds according to the invention, which are formulated as wettable powders or as emulsion concentrates, are sprayed at an application rate of 600 to 800 l of water/ha (converted) in a dosage stated in tables 1 to 5 onto the surface of the green plant parts. After the test plants have been left to stand in the greenhouse for 3 to 4 weeks under optimum growth conditions, the action of the compounds according to the invention is scored in comparison to compounds disclosed in the prior art. As shown by the results of these comparison tables, the selected compounds according to the invention have better herbicidal activity against a broad spectrum of economically important mono- and dicotyledonous harmful plants than the compounds disclosed in the prior art.

Meanings of the abbreviations used in the comparison tables below:

| | | | |
|---|---|---|---|
| ABUTH | *Abutilon theophrasti* | AMARE | *Amaranthus retroflexus* |
| AVEFA | *Avena fatua* | CYPES | *Cyperus serotinus* |
| DIGSA | *Digitaria sanguinalis* | ECHCG | *Echinochloa crus galli* |
| GALAP | *Galium aparine* | LOLMU | *Lolium multiflorum* |
| MATIN | *Matricaria inodora* | PHBPU | *Pharbitis purpureum* |
| POLCO | *Polygonum convolvulus* | SETVI | *Setaria viridis* |
| STEME | *Stellaria media* | VERPE | *Veronica persica* |
| VIOTR | *Viola tricolor* | XANST | *Xanthium strumarium* |

Comparative table 1:

| Compound No. | Dosage [g a.i./ha] | Activity against harmful plants | | |
|---|---|---|---|---|
| | | MATIN | POLCO | VIOTR |
| [structure] | 320 | 90% | 70% | 90% |

-continued

| Compound No. | Dosage [g a.i./ha] | Activity against harmful plants | | |
|---|---|---|---|---|
| | | MATIN | POLCO | VIOTR |
| Compound according to the invention 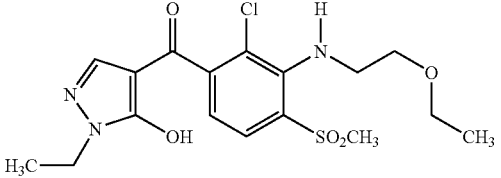 Compound known from WO 98/42678 | 320 | 0% | 0% | 70% |

Comparative table 2:

| Compound No. | Dosage [g a.i./ha] | Activity against harmful plants | | | |
|---|---|---|---|---|---|
| | | ECHCG | SETVI | POLCO | VERPE |
| 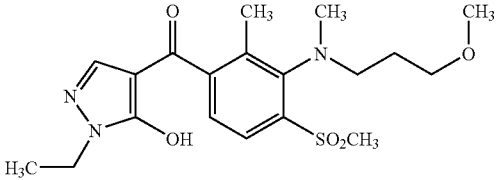 Compound according to the invention | 80 | 90% | 90% | 80% | 90% |
| 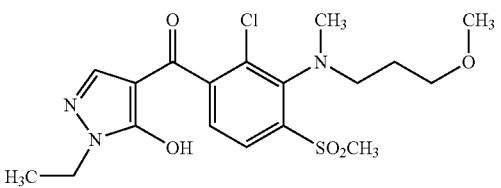 Compound known from WO 98/42678 | 80 | 40% | 0% | 30% | 60% |

Comparative table 3:

| Compound No. | Dosage [g a.i./ha] | Activity against harmful plants | |
|---|---|---|---|
| | | SETVI | VERPE |
| 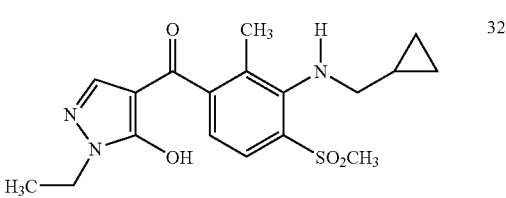 Compound according to the invention | 320 | 100% | 90% |

-continued

| Compound No. | Dosage [g a.i./ha] | Activity against harmful plants | |
|---|---|---|---|
| | | SETVI | VERPE |
| 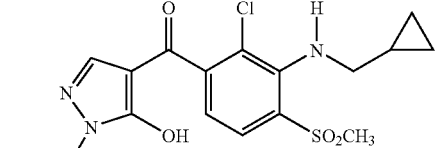 Compound known from WO 98/42678 | 320 | 80% | 70% |

The invention claimed is:

1. A 4-(3-aminobenzoyl)-1-ethylpyrazole of the formula (I), or a salt thereof

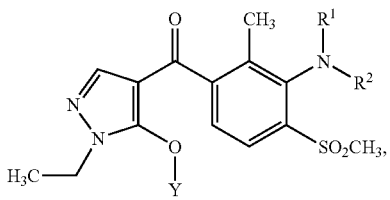

in which

R$^1$ is hydrogen, (C$_1$-C$_6$)-alkyl or (C$_1$-C$_4$)-alkoxy-(C$_1$-C$_6$)-alkyl, R$^2$ is (C$_1$-C$_6$)-alkyl, (C$_2$-C$_6$)-alkenyl, (C$_2$-C$_6$)-alkynyl, (C$_1$-C$_4$)-alkoxy-(C$_1$-C$_6$)-alkyl, di-(C$_1$-C$_4$)-alkoxy-(C$_1$-C$_6$)-alkyl, (C$_1$-C$_4$)-alkoxy-(C$_1$-C$_4$)-alkoxy-(C$_1$-C$_6$)-alkyl, (C$_3$-C$_6$)-cycloalkyl or (C3-C6)-cycloalkyl-(C$_1$-C$_6$)-alkyl;

Y is hydrogen, (C$_1$-C$_6$)-alkylsulfonyl, (C$_1$-C$_4$)-alkoxy-(C$_1$-C$_6$)-alkylsulfonyl, or is phenylsulfonyl, thiophenyl-2-sulfonyl, benzoyl, (C$_1$-C$_4$)-alkylbenzoyl-(C$_1$-C$_6$)-alkyl or benzyl, each of which is substituted by m identical or different radicals from the group consisting of halogen, (C$_1$-C$_4$)-alkyl and (C$_1$-C$_4$)-alkoxy, m is 0, 1, 2 or 3, with the proviso that (1-ethyl-5-hydroxy-1H-pyrazol-4-yl) [2-methyl-3-(methylamino)-4-(methylsulfonyl) phenyl]methanone, [3-(ethylamino)-2-methyl-4-(methylsulfonyl)phenyl](1-ethyl-5 -hydroxy-1H-pyrazol-4-yl) methanone, (1-ethyl-5-hydroxy-1H-pyrazol-4-yl)[2-methyl-4-(methylsulfonyl)-3-(propylamino) phenyl] methanone, (1-ethyl-5-hydroxy-1H-pyrazol-4-yl){2-methyl-3-[(1-methylethyl)amino]-4-(methyl-sulfonyl) phenyl}methanone, [3-(butylamino)-2-methyl-4-(methylsulfonyl)phenyl](1-ethyl-5-hydroxy-1H-pyrazol-4-yl) methanone, (1-ethyl-5-hydroxy-1H-pyrazol-4-yl) {3-[(2-methoxyethyl)amino]-2-methyl-4-(methylsulfonyl)phenyl}methanone, [3-(cyclopropylamino)-2-methyl-4-(methylsulfonyl)phenyl](1-ethyl-5-hydroxy-1H-pyrazol-4-yl) methanone, (1-ethyl-5-hydroxy-1H-pyrazol-4-yl)[2-methyl-4-(methylsulfonyl)-3-(prop-2-en-1-ylamino) phenyl]methanone and [3-(dimethylamino)-2-methyl-4-(methylsulfonyl)phenyl](1-ethyl-5-hydroxy-1H-pyrazol-4-yl) methanone are excluded.

2. The 4-(3-aminobenzoyl)-1-ethylpyrazole of the formula (I), or a salt thereof, as claimed in claim 1 in which R$^1$ is hydrogen or (C$_1$-C$_4$)-alkyl, R$^2$ is (C$_1$-C$_4$)-alkyl, (C$_1$-C$_4$)-alkoxy-(C$_1$-C$_4$)-alkyl, di-(C$_1$-C$_2$)-alkoxy-(C$_1$-C$_4$)-alkyl, (C$_1$-C$_4$)-alkoxy-(C$_1$-C$_4$)-alkoxy-(C$_1$-C$_4$)-alkyl, (C$_3$-C$_6$)-cycloalkyl or (C$_3$-C$_6$)-cycloalkyl-(C$_1$-C$_2$)-alkyl;

Y is hydrogen, (C$_1$-C$_3$)-alkylsulfonyl, (C$_1$-C$_2$)-alkoxy-(C$_1$-C$_4$)-alkylsulfonyl, or is phenylsulfonyl, thiophenyl-2-sulfonyl, benzoyl, (C$_1$-C$_4$)-alkylbenzoyl-(C$_1$-C$_6$)-alkyl or benzyl, each of which is substituted by m methyl groups, m is 0 or 1.

3. The 4-(3-aminobenzoyl)-1-ethylpyrazole of the formula (I), or a salt thereof, as claimed in claim 1 in which R$^1$ is hydrogen or (C$_1$-C$_4$)-alkyl, R$^2$ is (C$_1$-C$_4$)-alkyl, (C$_1$-C$_4$)-alkoxy-(C$_1$-C$_4$)-alkyl, di-(C$_1$-C$_2$)-alkoxy-(C$_1$-C$_4$)-alkyl, (C$_1$-C$_4$)-alkoxy-(C$_1$-C$_4$)-alkoxy-(C$_1$-C$_4$)-alkyl, (C$_3$-C$_6$)-cycloalkyl or (C$_3$-C$_6$)-cycloalkyl-(C$_1$-C$_2$)-alkyl;

Y is hydrogen.

4. A herbicidal composition which comprises a herbicidally effective amount of at least one compound of the formula (I), or a salt thereof, as claimed in claim 1.

5. The herbicidal composition as claimed in claim 4 as a mixture with formulation auxiliaries.

6. A method for controlling unwanted plants which comprises applying an effective amount of at least one compound of the formula (I), or a salt thereof, as claimed in claim1 to a plant or a site of unwanted plant growth.

7. A method for controlling unwanted plants comprising applying an effective amount of a herbicidal composition as claimed in claim 4 to a plant or a site of unwanted plant growth.

8. A method as claimed in claim 7 wherein the compounds of the formula (I), or a salt thereof, are used for controlling unwanted plants in crops of useful plants.

9. A method as claimed in claim 8 wherein the useful plants are transgenic useful plants.

10. A 4-(3-aminobenzoyl)-1-ethylpyrazole of the formula, or a salt thereof, (I) as claimed in claim 1 wherein when Y is hydrogen, the compounds of the formula (I) may occur in different tautomeric structures:

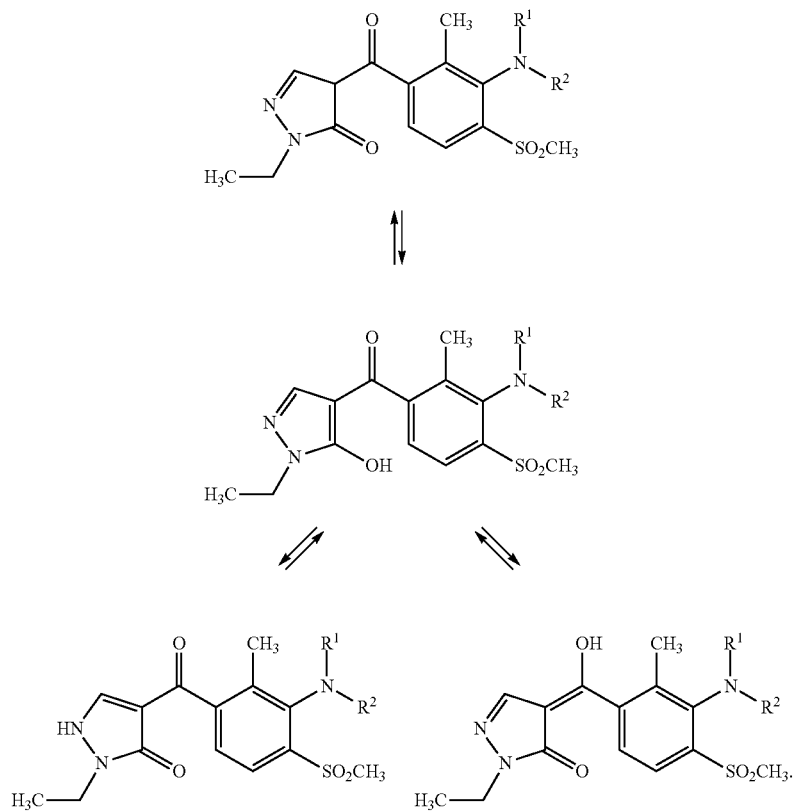

11. A 4-(3-aminobenzoyl)-1-ethylpyrazole of the formula (I), or a salt thereof, as claimed in claim 1 wherein said 4-(3-aminobenzoyl)-1-ethylpyrazole contains an acidic proton that is removed by reaction with a base.

12. A 4-(3-aminobenzoyl)-1-ethylpyrazole of the formula (I), or a salt thereof, as claimed in claim 11, wherein said acidic proton is removed from a base that comprises at least one selected from the group consisting of hydrides, hydroxides, carbonates of lithium, sodium, potassium, magnesium and calcium, and ammonia and organic amines.

13. A 4-(3-aminobenzoyl)-1-ethylpyrazole of the formula (I), or a salt thereof, as claimed in claim 1 which is present in the form of a salt formed by an adducts with an organic acid.

14. A 4-(3-aminobenzoyl)-1-ethylpyrazole of the formula (I), or a salt thereof, as claimed in claim 1 which is present as stereoisomers and/or mixtures thereof.

15. A 4-(3-aminobenzoyl)-1-ethylpyrazole of the formula (I), or a salt thereof, as claimed in claim 1, wherein Y comprises hydrogen.

16. A 4-(3-aminobenzoyl)-1-ethylpyrazole of the formula (I), or a salt thereof, as claimed in claim 1, wherein $R^1$ comprises hydrogen or methyl.

17. A 4-(3-aminobenzoyl)-1-ethylpyrazole of the formula (I), or a salt thereof, as claimed in claim 1, wherein $R^2$ comprises —$(CH_2)_3$—O—$CH_3$.

18. A 4-(3-aminobenzoyl)-1-ethylpyrazole of the formula (I), or a salt thereof, as claimed in claim 1, wherein
Y is hrydrogen;
$R^1$ is hydrogen; and
$R^2$ is —$(CH_2)_3$—O—$CH_3$.

19. A 4-(3-aminobenzoyl)-1-ethylpyrazole of the formula (I), or a salt thereof

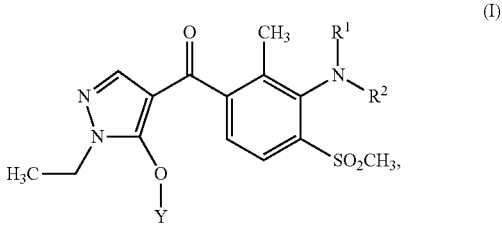

in which $R^1$ is hydrogen, $(C_1$-$C_6)$-alkyl or $(C_1$-$C_4)$-alkoxy-$(C_1$-$C_6)$-alkyl, $R^2$ is $(C_1$-$C_6)$-alkyl, $(C_2$-$C_6)$-alkenyl, $(C_2$-$C_6)$-alkynyl, $(C_1$-$C_4)$-alkoxy-$(C_1$-$C_6)$-alkyl, di-$(C_1$-$C_4)$-alkoxy-$(C_1$-$C_6)$-alkyl, $(C_1$-$C_4)$-alkoxy-$(C_1$-$C_4)$-alkoxy-$(C_1$-$C_6)$-alkyl, $(C_3$-$C_6)$-cyclo alkyl or $(C_3$-$C_6)$-cycloalkyl-$(C_1$-$C_6)$-alkyl;

Y is $(C_1$-$C_6)$-alkylsulfonyl, $(C_1$-$C_4)$-alkoxy-$(C_1$-$C_6)$-alkylsulfonyl, or is phenylsulfonyl, thiophenyl-2-sulfonyl, benzoyl, $(C_1$-$C_4)$-alkylbenzoyl-$(C_1$-$C_6)$-alkyl or benzyl, each of which is substituted by m identical or different radicals from the group consisting of halogen, $(C_1$-$C_4)$-alkyl and $(C_1$-$C_4)$-alkoxy, and m is 0, 1, 2 or 3.

20. A 4-(3-aminobenzoyl)-1-ethylpyrazole of the formula (I), or a salt thereof

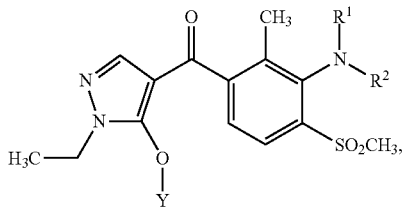

in which
R$^1$ is hydrogen, (C$_1$-C$_6$)-alkyl or (C$_1$-C$_4$)-alkoxy-(C$_1$-C$_6$)-alkyl,
R$^2$ is (C$_2$-C$_6$)-alkynyl, di-(C$_1$-C$_4$)-alkoxy-(C$_1$-C$_6$)-alkyl, (C$_1$-C$_4$)-alkoxy-(C$_1$-C$_4$)-alkoxy-(C$_1$-C$_6$)-alkyl;
Y is hydrogen, (C$_1$-C$_6$)-alkylsulfonyl, (C$_1$-C$_4$)-alkoxy-(C$_1$-C$_6$)-alkylsulfonyl, or is phenylsulfonyl, thiophenyl-2-sulfonyl, benzoyl, (C$_1$-C$_4$)-alkylbenzoyl-(C$_1$-C$_6$)-alkyl or benzyl, each of which is substituted by m identical or different radicals from the group consisting of halogen, (C$_1$-C$_4$)-alkyl and (C$_1$-C$_4$)-alkoxy, and m is 0, 1, 2 or 3.

* * * * *